US006830149B2

United States Patent
Merboth et al.

(10) Patent No.: US 6,830,149 B2
(45) Date of Patent: Dec. 14, 2004

(54) PACKAGE WITH INSERT FOR HOLDING ALLOGRAFT IMPLANT TO PRECLUDE LIPID TRANSFER

(75) Inventors: Barbara L. Merboth, Bridgewater, NJ (US); Malcolm Will, Aberdeen, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 7 days.

(21) Appl. No.: 10/092,489

(22) Filed: Mar. 8, 2002

(65) Prior Publication Data

US 2003/0168370 A1 Sep. 11, 2003

(51) Int. Cl.[7] .............................................. A61B 17/06
(52) U.S. Cl. ...................................... 206/438; 206/461
(58) Field of Search .............................. 206/438–440, 206/461, 570–572

(56) References Cited

U.S. PATENT DOCUMENTS

| | | | |
|---|---|---|---|
| 4,697,703 A | 10/1987 | Will | |
| 4,736,850 A | * 4/1988 | Bowman et al. | 206/570 |
| 4,750,619 A | 6/1988 | Cohen et al. | |
| 5,176,258 A | 1/1993 | Antal | |
| 5,193,679 A | * 3/1993 | White | 206/438 |
| 5,257,692 A | 11/1993 | Heacox | |
| 5,615,770 A | 4/1997 | Applebaum et al. | |
| 5,690,226 A | 11/1997 | N'Guyen | |
| 5,720,391 A | 2/1998 | Dohm et al. | |
| 5,868,253 A | * 2/1999 | Krueger et al. | 206/438 |
| 6,012,580 A | 1/2000 | Peters et al. | |
| 6,039,183 A | * 3/2000 | Rudnick et al. | 206/570 |
| 6,622,864 B1 | * 9/2003 | Debbs et al. | 206/438 |

* cited by examiner

Primary Examiner—Jim Foster
(74) Attorney, Agent, or Firm—John S. Hale; Gipple & Hale (57) ABSTRACT

A double sterile container assembly for storing sterile allograft tissue implant forms constructed with an outer container defining an open faced cavity and a flange extending outward from the cavity and a stepped recess formed in the flange surrounding said cavity. An inner container sized to fit in the open faced cavity also defines an open faced cavity and a flange extending outward from the cavity with the inner container flange being of a dimension to fit into the stepped recess of the outer container. An insert retainer sized to fit into the inner container cavity defines a shaped structure therein to hold a tissue implant form. A permeable cover is sealed to the flange of the inner container covering the inner container cavity; and an outer cover is sealed to the flange of the outer container covering outer container cavity to form a double sterile implant container assembly.

11 Claims, 6 Drawing Sheets

PACKAGE WITH INSERT FOR HOLDING ALLOGRAFT IMPLANT TO PRECLUDE LIPID TRANSFER

CROSS-REFERENCE TO RELATED APPLICATIONS

There are no other applications related to the present application.

TECHNICAL FIELD OF THE INVENTION

The present invention generally relates to packaging for sterile tissue specimens for use in tissue transplant and more specifically to packages for allograft implant tissue forms in specifically designed sterile packages or containers which prevent lipid collection around the implant form.

BACKGROUND OF THE PRIOR ART

Allograft tissue forms are useful in orthopaedic and neurosurgery. In practice, processed human tissue is delivered to the hospital and eventually to the surgeon in a form useful for surgical implantation in a sterile package. Unfortunately, while large amounts of time have been spent on development and processing of the tissue implant form, little consideration has been spent on the package design and the specific problems involved with packaging bone implant forms constructed of demineralized, partially demineralized or mineralized bone. Packaging that is currently used for bone implant forms is cumbersome and it is often difficult to easily remove the implant form from such packaging while wearing gloves during a surgical procedure. Furthermore a need has developed for a simple, inexpensive packaging that may be used to safely retain implant allograft forms in a sterile condition away from the lipid pooling while allowing storage of same and maintaining sterility up until the actual time of implantation during surgery.

There are presently available a number of kinds of packaging for sterile specimens. One form of commonly used packaging is to provide the allograft tissue in a freeze-dried state in a glass bottle with a stopper or other waterproof container. This type of packaging provides the advantage of stabilizing the tissue for storage in a warehouse or hospital supply room at normal room-temperature conditions. Freeze-dried packaging works effectively for relatively small sizes of allograft tissues such as demineralized bone powders, chips, and small machined shapes such as pins, screws and spinal spacers.

Another form of packaging which has been used for holding products such as a pre-sterilized medical devices and allograft implant forms are sealed blister containers. Such containers generally comprise a relatively rigid blister tray with a peripheral flange and a foil composite material or paper backing sheet positioned over the open tray in overlapping engagement with the peripheral flange forming a cover. The cover is manually peeled-away from the flange to which it is sealed to allow access to the medical device or implant tissue form contained therein. Other examples of packaging for medical devices or implant forms which have been utilized or are known in the art are shown in the following patents.

U.S. Pat. No. 6,012,580 is directed toward a clamshell type package with two halves pivoted together at a hinge constructed of a transparent plastic constituted to serve as a universal package for implant materials.

U.S. Pat. No. 5,720,391 shows a blister package and insert holder for a heart valve prosthesis. The package is constructed with an outer tray which receives an inner tray. An inner tray lid seals the inner tray and is provided with a pull tab on its exterior surface so that the same can be pulled away from the lip of the inner tray for access to the sterile heart valve prosthesis. The outer tray is provided with a tray lid which is sealed to the lip of an outer flange of the outer tray.

U.S. Pat. No. 5,690,226 shows a sealed air tight molded blister package of PETG having a hollow interior with the opening surrounded by an outwardly extending flange. A multi-layer peelable cover is sealed to the flange surrounding the opening. The cover and the flange are deformed towards the bottom of the container from the plane of the opening sealed by the peelable cover.

U.S. Pat. No. 5,615,770 discloses a sterilizable medical implant package insert placed within a standard sterile implant package holding an implant and allowing for the automatic presentation of the implant from the insert when the sterile package top is opened.

U.S. Pat. No. 5,257,692 is directed toward a three envelope package for preserving tissue specimens or other sterile objects. The sterile tissue sample is sealed within an innermost envelope which is sterile inside and outside. The innermost envelope is sealed within the sterile interior of an intermediate envelope which is both sterile inside and outside. This intermediate envelope is made of foil or another substance impermeable to a storage medium such as liquid nitrogen and is sealed within the sterile interior of an outermost envelope made of foil or another substance impermeable to a storage medium. The outermost envelope provides complete impermeability to liquid nitrogen, eliminating the possibility of nitrogen seepage through the peel-baked seal of the intermediate envelope.

U.S. Pat. No. 5,176,258 shows a package with a peripheral flange around a blister defining an open cavity for receiving a product and a compressible insert for securing the product against movement in the package cavity. At least one projection on the insert extends laterally from the cavity over the peripheral flange and a lid covering the cavity is continuously sealed to the peripheral flange and the projection along a single seal.

U.S. Pat. No. 4,750,619 is directed toward a package for a sterile prosthetic implant element comprising an outer receptacle and an inner receptacle which fits into the cavity of the outer receptacle. Both of the receptacles are provided with outwardly extending flanges surrounding the outer periphery of the cavity of each receptacle and receive a lid which is secured thereto. A tray received within the inner receptacle has hinged leaves so that upon placement of the tray within the receptacle and folding the hinged leaves, the prosthetic implant element is confined within a defined envelope to protect the same against damage.

U.S. Pat. No. 4,697,703 discloses a double sterile package for medical items such as a hip joint prosthesis with an outer open container enclosing an inner package containing the medical item. The inner package has a first insert contained in the open top container, a lid and a second insert carried by the lid. The outer container is sealed with a cover which engages an outer peripheral flange formed around the open top of the outer container.

None of the above noted packages are conducive to implants formed of bone and other tissue. Animal bone tissue forms, after processing, include lipids sometimes called structural fats. Lipids are a group of fatty substances that include fatty oils, waxes, sterols such as cholesterol, triglycerides (the principal forms of fat in body fat) and esters of fatty acids containing groups such as phosphoric acid (phospholipids) and carbohydrates (glycolipids). Over time, the fatty oils contained in the processed bone material are drawn out of the bone and are absorbed by the permeable cover and begin to dissolve the adhesive bond between the cover and the container. This activity causes the cover to separate from the container receptacle destroying the sterility of the package and leaving pools or rivets of a dark oily material which is unsightly and causes the surgeon to discard or send back the tissue form. This lipid migration is a serious problem for manufacturers of forms of allograft bone, and presents problems for the hospital and surgeon user. Accordingly, a double sterile package container assembly has been developed to handle bone implant forms of allograft tissue which resolves these problems.

SUMMARY OF THE INVENTION

The present invention is directed toward an allograft tissue package constructed to hold allograft bone tissue implant forms in a sterile inner package allowing drainage of the lipids contained in the implant without destroying the seal and sterility of the package. The package for storing sterile allograft tissue implant forms is constructed with an outer container defining an open faced cavity and a flange extending outward from said cavity with a stepped recess formed in said flange surrounding the cavity. An inner container which is adapted to be seated in the cavity of the outer container defines an open faced cavity and a flange extending outward from said cavity, the inner container flange being of a dimension to fit into the stepped recess of the outer container. An insert member sized to fit into said inner container cavity defines a shaped depression thereinto hold a tissue implant form within a designated space defined by the shaped depression.

The inner container is covered by a permeable cover sealed to the flange of the inner container allowing the tissue form to be treated and the outer container is covered by an impermeable cover sealed to the flange of the outer container covering the outer container cavity.

It is an object of the invention to provide a packaging system which holds specially constructed tissue forms in a double sterile condition which allows a user to peel away a cover to reach the inner tissue container and then peel away a cover to provide access to the tissue form.

It is yet another object to provide a sterile package for implant forms up to the point where the implant is presented to the surgeon for implant.

It is another object of the invention to provide a medical package in which an implant tissue form can be maintained in a double sterile condition.

It is still another object of the invention to provide a package for storing sterile tissue implant forms for later use in an implant situation.

It is yet another object of the invention to provide a package for storing tissue implant forms whereby the tissue implants forms can be removed from the package in a sterile condition.

It is still another object of the invention to provide a sterile tissue package which allows treatment of the tissue form while it is contained in a sterile package.

It is yet another object of the invention to provide a sterile tissue package which can be stored for treatment in a position that saves package space within the treatment apparatus.

In the accompanying drawings, there is shown illustrative embodiments of the invention from which these and other objectives, novel features and advantages will be readily apparent.

DETAILED DESCRIPTION OF THE INVENTION

The preferred embodiment and best mode of the tissue form package invention is shown in FIGS. 1, 2 and 4–9. In the preferred embodiment of the present invention thin, plastic material is used that is sterilizable and that can be formed by any suitable method such as for example, injection molding, pressure molding, vacuum forming and the like. The component material used for the outer container 20 of the allograft bone tissue package assembly 10 is preferably made in the form of a laminate made of an available material such as polyethylene terephthalateglycol (PETG) (a copolyester made by Eastman Chemical) as the inside layer, with the outside layer being another available material polycholrotrifluoroethylene (PCTFE) under the trademark ACLAR (a fluorinated-chlorinated thermoplastic made by Allied Corporation) which is impermeable to oxygen and other atmospheric gases and which is a highly moisture resistant barrier. Other suitable plastics which can be used for the outer container which work under the low temperature treatment conditions are low-density polyethylene, high-density polyethylene, cross-linked, high-density polyethylene, polycarbonate, polysulfone, fluorinated ethylene polypropylene, ethylene-tetratluoroethylene, ethylene-chlorotritluoroethylene copolymer, perfluoroalkoyl, polyurethane.

Figure 1:
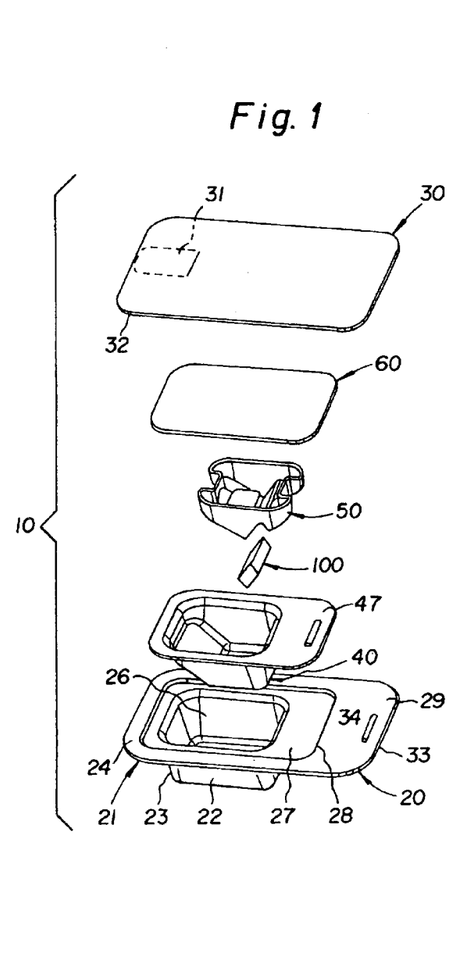
FIG. 1 is an exploded perspective view of the inventive double sterile allograft tissue package with insert and tissue implant form contained therein.
Figure 2:
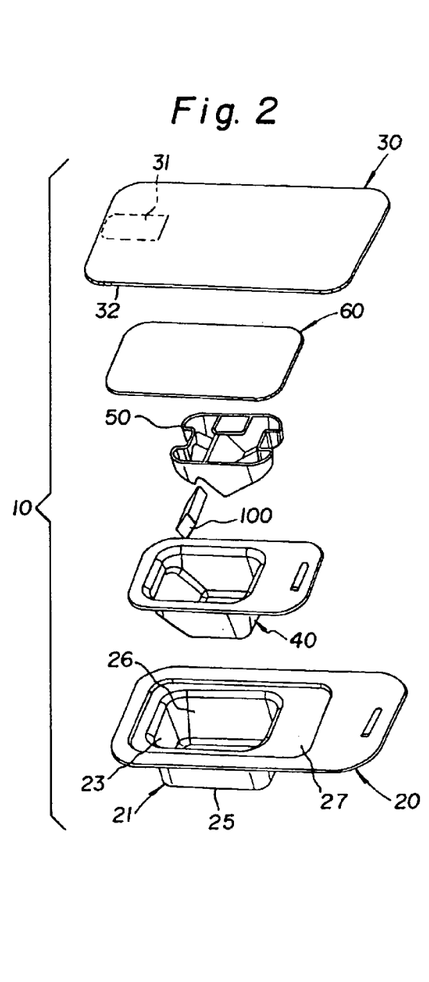
FIG. 2 is an exploded perspective view of the tissue package of FIG. 1 with the retainer insert reversed in the inner container.

The outer container 20 has a blister body 21 integrally formed with side walls 22, end walls 23 and a base 25 which together define an open faced cavity or chamber 26. The top sections of the walls 22 and 23 end in a flat or planar peripheral flange portion 24 which is substantially parallel to the base 25. A stepped recess 27 is formed in the flange portion 24 and is disposed around the open cavity 26. The stepped recess 27 is configured to hold a corresponding flange 47, 147 of an inner container 40, 140. The outer edge 28 of recess 27 is beveled upward to an upper planar surface 29 which supports and holds cover 30. The lid or cover 30 is sized and configured to cover the recess 27 in its entirety and is seated on the upper surface of planar surface 29 continuously around the recess 27 so that the peripheral edge 32 of the cover 30 is substantially aligned in overlapping fashion with the peripheral edge 33 on the planar surface 29. The cover 30 is preferably an impermeable aluminum foil commercially available in 1 to 2 mil thickness sizes which bears product information and can be provided with a pull tab 31. The outer container upper flange planar surface 29 has one section extended to form a handle portion 34.

An inner insert container 40, is molded from the PETG plastic or the ACLAR/PETG laminate noted above is constructed so that it can be placed in the cavity 26 of the outer container 20. The inner insert container 40 comprises a blister body 41 formed with integral side walls 42, end walls 43 and 44 and a base 45 which together form a cavity 46. The top edges of side walls 42 and end walls 43 and 44 end in a flange 47 with a planar surface which extends outward from cavity 46 with one end flange portion 48 extending outward from the cavity 46 a greater distance than the other flange portion to form a handle. The configuration and thickness of the flange planar surface of the blister container is such that it fits in recess 27 of the outer container 20 and is supported by the upper surface of the recess so that its upper surface is substantially parallel to the plane of the upper flange surface of flange 24. Insert container end wall 44 has an angled planar portion 49 which can provide a seat upon which the inner insert container 40 is placed during the freeze drying stage. This seat also allows an increased number of filled inner insert containers 40 to be placed on the shelf of the freezer apparatus as it takes up less space than a container placed on its base. The angled planar portion 49 is angled from 30 degrees to 45 degrees from the plane of the base 45 preferably at around 45 degrees.

Figure 5A:
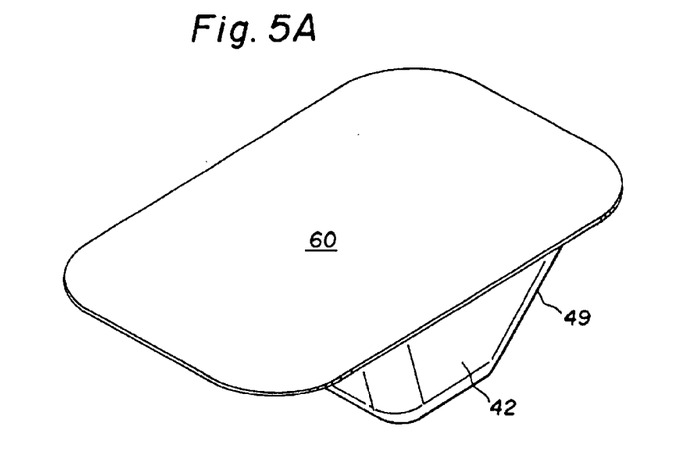
FIG. 5A is a perspective view of the inner container with cover.
Figure 5B:
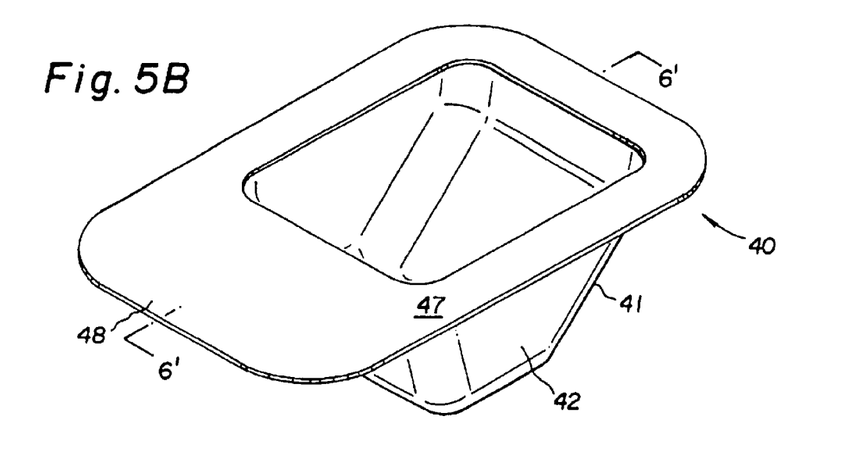
FIG. 5B is a perspective view of the inner container with cover and insert retainer removed.

A cover 60 as shown in FIG. 5A is sealed to the surface of flange 47 once the retainer insert 50 with the allograft bone implant form 100 has been inserted into the cavity 46. The material selected for the cover 60 of the inner container 40 is preferably made from a porous, steam penetrable or pervious to a sterilizing agent such as ethylene oxide such as a spun bonded polyolefin material having sterile barrier properties, as for example TYVEK a material available from Dupont de Nemours. The construction of inner containers 40 and 140 keeps the bone material of the implant form away from the TYVEK or paper (cellulose) water permeable paper and lipids retained therein while keeping bacteria out.

Figures 6, 7, 8:
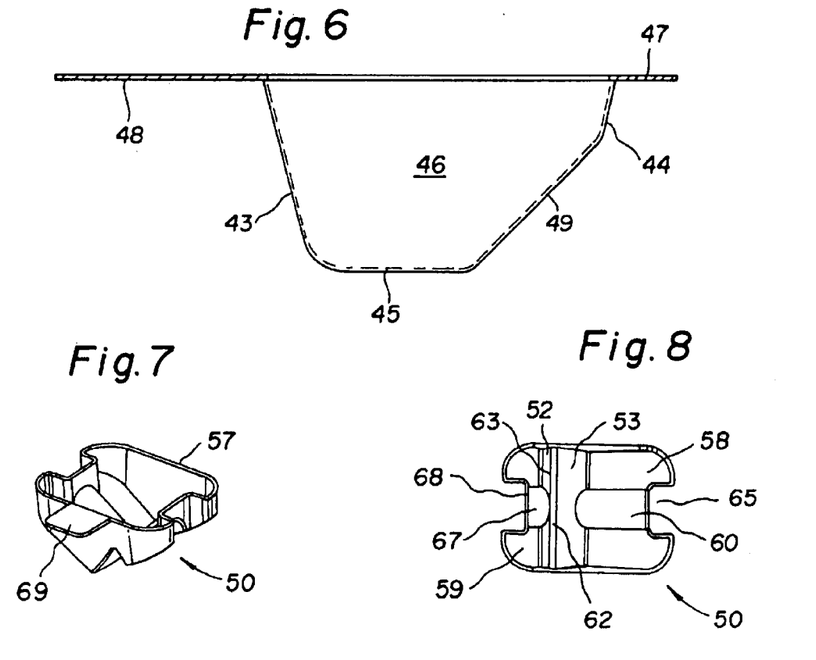
FIG. 6 is a cross section of the inner container shown in FIG. 5B taken along line 6'—6'.
FIG. 7 is a perspective view of a channeled retainer insert for holding a shaped tissue implant in the inner container of FIGS. 5A and 5B.
FIG. 8 is a bottom plan view of the retainer insert of FIG. 7.
Figure 9:
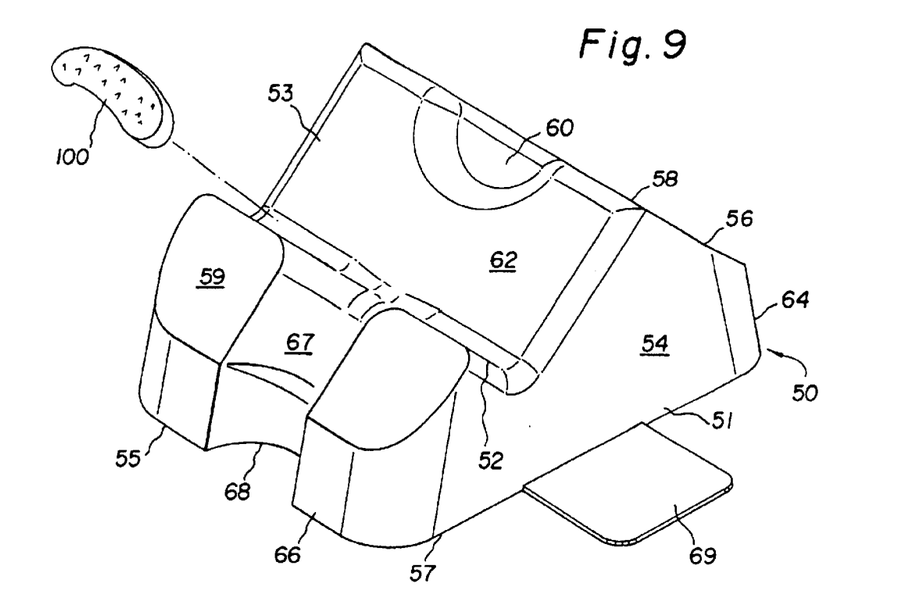
FIG. 9 is an enlarged bottom perspective view of the retainer insert of FIG. 8.

The tissue form holding retainer insert 50 constructed of PETG as shown in FIGS. 7–9 is adapted to hold shaped bone tissue implant forms. The retainer insert 50 has an external configuration so that the same can be mounted in the cavity 46 to hold the tissue form in a substantially fixed or retained condition within the inner container 40. The retainer insert 50 is constructed with a housing 51 defining a trough 52 with angled side walls running from one side 53 of the retainer insert body to the other side 54 across the width of the retainer insert 50. Two sets of upwardly angled planar faces on the top of the insert body run respectively from ends 55 and 56 of the insert body and intersect the respective side walls forming the trough at the top of the trough 52. The two angular faces, maximum planar faces 58 and minimum planar faces 59 run from the ends 56 and 55 respectively and intersect the top of the trough 52 and are angled downward. A semi-circular groove 60 divides the maximum planar faces 58 and intersects a major side wall 62 of the tough 52 at one end and leads into a notch or recess 65 cut or formed from the base 57 up along planar end wall 64 of end 56. A semi-cylindrical groove 67 divides the minimum planar faces 59 and intersects a minor side wall 63 of the tough 52 around the midpoint of the trough. The other end of groove 67 leads into a notch or recess 68 formed from the base 57 up along a planar end wall 66 of end 55. A lift tab 69 is formed integrally with or secured to side 54 and extends outward from the side 54. The lift tab can be located outwardly as shown in FIG. 7 or inwardly as shown in FIG. 2.

An alternate tissue holding insert embodiment 140 as shown in FIGS. 3 and 10–12 is adapted to hold a cylindrical shaped bone tissue implant 104 and is configured to hold the tissue implant form in a substantially fixed or retained condition during transportation and storage of the assembly 10.

Figure 10:
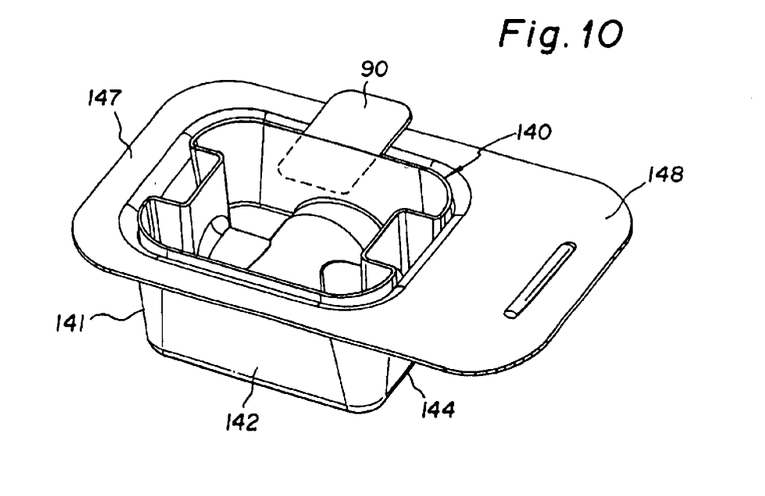
FIG. 10 is a enlarged perspective view of another inner container embodiment with cover removed and a retainer insert for holding cylindrically shaped tissue implants.
Figure 11:
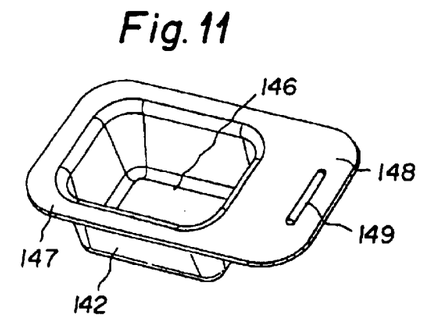
FIG. 11 is a perspective view of the inner container of FIG. 10 with retainer insert removed.
Figure 12:
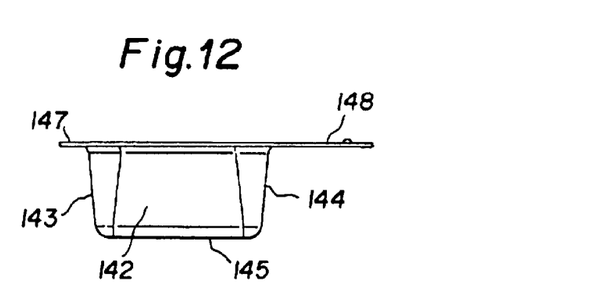
FIG. 12 is a side elevational view of the side of the inner container of FIG. 11.

The inner insert container 140, molded from the PETG plastic or the ACLAR/PETG laminate noted above is constructed so that it can be placed in the cavity 26 of the outer container 20. The inner insert container 140 comprises a blister body 141 formed with integral side walls 142, end walls 143 and 144 and a base 145 which together form an implant form cavity 146. The top edges of side walls 142 and end walls 143 and 144 form a flange 147 with a planar surface which extends outward from cavity 146 with one end flange portion 148 extending outward from the cavity 146 a greater distance than the other flange portions to form a handle. A rib 149 is formed on flange portion 148 to aid in removal of the cover. Cover 150 is sealed over the flange areas 147 and 148 covering cavity 146 to place the inner container 140 in a sealed sterile condition. The cover 92 is preferably made from TYVEK or other suitable permeable material. The configuration and thickness of the flange planar surface of the blister container is such that it fits in recess 27 of the outer container 20 and is supported by the upper surface of the recess.

Figure 3:
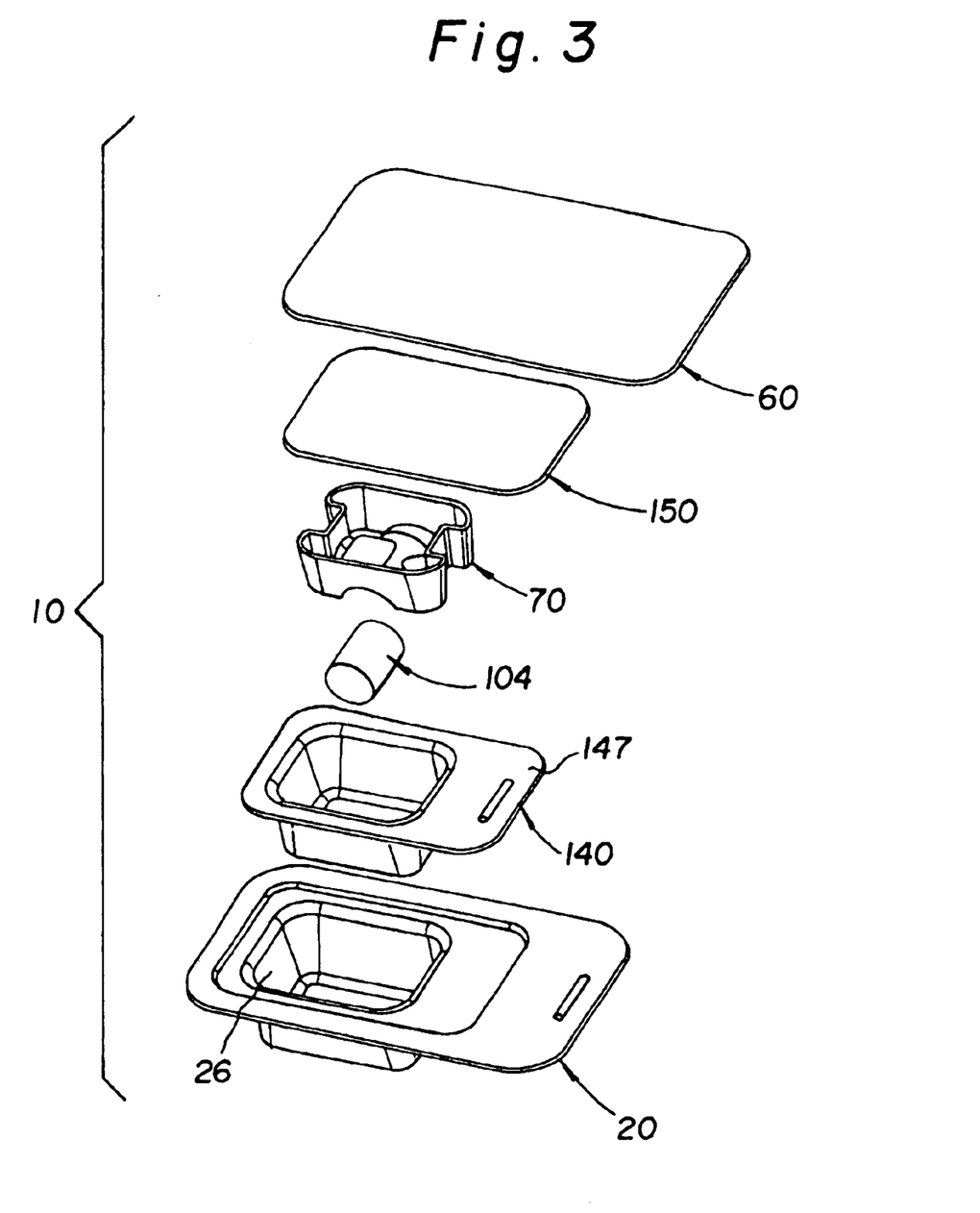
FIG. 3 is an exploded perspective view of a double sterile tissue package for a cylindrical tissue implant form.
Figure 4:
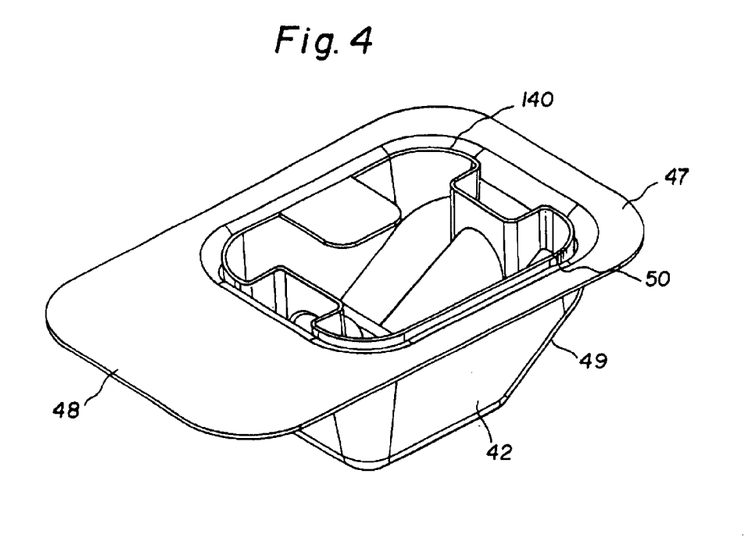
FIG. 4 is a perspective view of the inner container with cover removed and insert retainer mounted therein.
Figures 13, 14, 15:
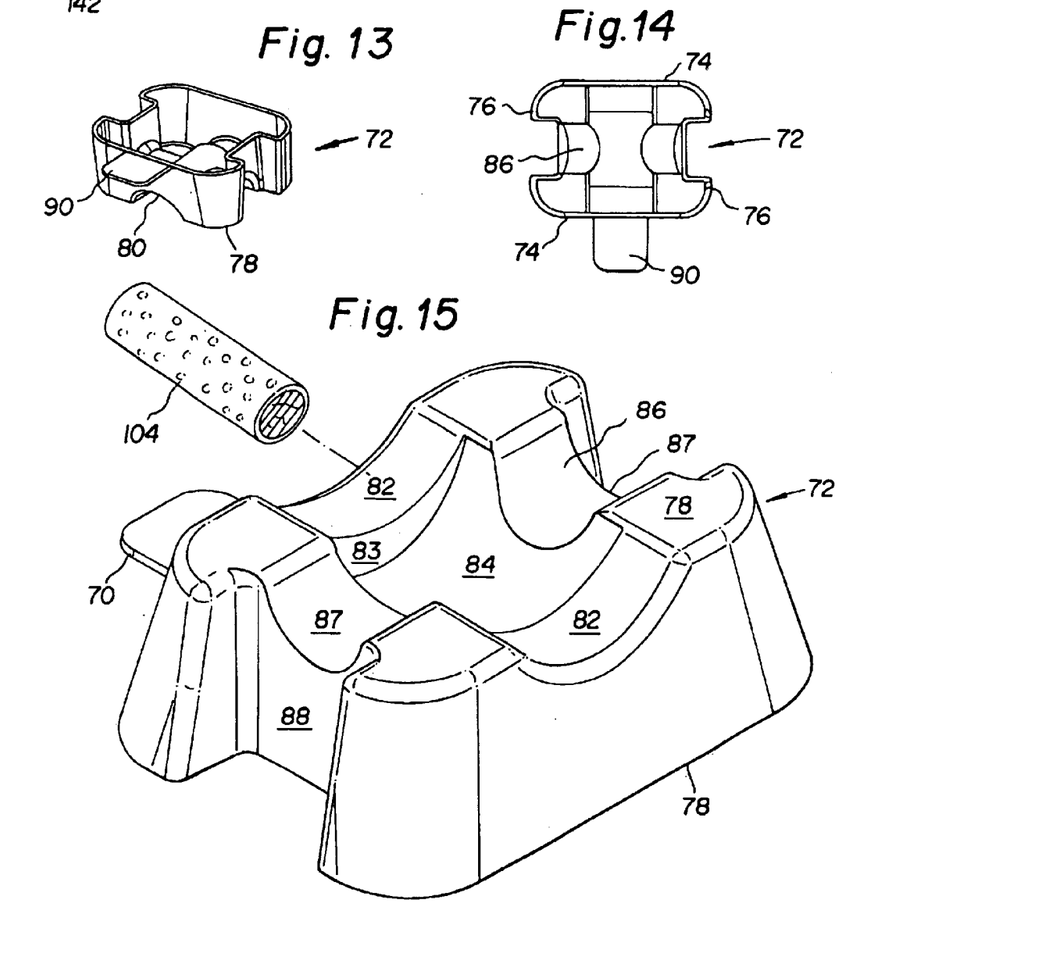
FIG. 13 is a perspective view of the cylindrically shaped tissue implant retainer insert for holding a cylindrically shaped tissue implant form.
FIG. 14 is a bottom plan view of the retainer insert of FIG. 13.
FIG. 15 is an enlarged bottom perspective view of the retainer insert of FIG. 13.

A retainer insert 70 for this embodiment is shown in FIGS. 13–15 and is formed with a housing 72 having side walls 74, end walls 76 and a base 78 which defines a cavity 79. The housing 72 is formed with a semicircular channel or depression 80 extending from one side wall 74 to the other side wall 74a. The channel 80 has a step 82 formed on each end forming a shoulder 83 which terminates at a lower semicircular channel section 84 of the channel 80. Channel section 84 has a length which is the same or slightly greater than the length of the circular implant form 104 which is to be placed therein. Each end of the circular bone implant form 104 is restrained from sliding movement by shoulders 83 of steps 82 which acts as a stop holding the bone implant form 104 in position. A second channel 86 is formed in the housing 72 and runs between the end walls 76 substantially transverse to and intersecting channel 80. The ends 87 of channel 86 terminate at notches or recesses 88 formed at approximately the midpoint of the end walls 76. The notches or recesses 88 run from the base of the insert housing 72 to the top of the insert housing 72. A lift tab 90 is formed on the edge of a side wall 74 and extends outward. Alternatively the lift tab 90 can extend inwardly as shown in FIG. 3. The insert channels 52, 60, 67, 84 and 86 are used for water and lipid removal when the tissue form is being lopidized.

After sealing of the cover 60, the package assembly 10 can be sterilized by radiation sterilization techniques.

In the assembly of the invention, the implant tissue form 100, 104 sits inside the respective tissue retainer insert 50, 70 and is placed inside the cavity 46, 146 of the inner container 40, 140 so that the tissue form is held in place against the walls of the inner container. The inner container is has a cover heat sealed thereto and is placed in the cavity of the outer container. A cover is heat sealed to the PETG surface. The package has formed channels to allow moisture to escape during the freeze drying process while keeping the tissue form in a sterile condition. The package can be subjected to multiple freeze-thaw cycles through the very large temperature excursion required by the use of $-80°$ C. freezing conditions. The temperature range change effecting the package could be as much as $110°$ C., from a $-80°$ C. freezer to a $+30°$ C. warehouse or storeroom area where the tissue may be selected for surgical use.

The packaging is easily disassembled during surgery because the trays are not fastened together and the removal of the outer container cover and inner container cover presents the top of th insert retainer allowing the same to be removed from the inner container. In addition using a clear packaging provides product visibility allowing easy identification of the product. Furthermore the packaging of the present invention provides dual sterile barriers in a recyclable container.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present inventions defined by the following claims.

What we claim is:

1. A container assembly for storing sterile allograft tissue implant forms in a sterile condition comprising:
   an outer container defining an open faced cavity and a flange extending outward from said cavity, a stepped recess formed in said flange surrounding said cavity;
   an inner container defining a base, walls integrally formed with said base, said wails defining an open faced cavity and a flange extending outward from said cavity, said inner container flange being of a dimension to fit into said stepped recess of said outer container,
   a one piece insert member sized to fit into said inner container cavity and removable from said inner cavity, said insert member defining a linear shaped structure therein to hold a tissue implant form adjacent said inner container base, said shaped structure defining a semicircular groove with shaped end portions which act as a retainer to seat a cylindrically shred tissue implantation form;
   a permeable cover sealed to the flange of the inner container covering said inner container cavity; and
   an outer cover sealed to the flange of the outer container covering said outer container cavity.

2. A container assembly as claimed in claim 1 wherein said insert member housing includes a lift tab extending from a side wail.

3. A container assembly as claimed in claim 1 wherein said inner container cover includes a tab for grasping to remove the inner cover from the flange of said inner container.

4. A container assembly as claimed in 1 wherein insert member housing defines recesses formed in end walls of said housing which intersect said groove positioned transverse said semicircular groove with stepped end portions.

5. A container assembly as claimed in claim 1 wherein said inner container has a housing defining an open faced cavity and a flange extending outward from said cavity, said housing comprising a front end wall, side walls connected to said front end wall and an angularly oriented planar rear end wall, all of said walls being integrally connected with a base to form an interior cavity adapted to hold an insert member.

6. A container as claimed in claim 1 wherein said outer container has a laminated body with an inner layer of polyethylene terephthalateglycol and an outer layer of ACKLAR.

7. A double sterile package container for storing sterile allograft tissue implant forms comprising:
   an outer container defining an open faced cavity and a flange extending outward from said cavity, a stepped recess formed in said flange surrounding said cavity;
   an inner container defining an open faced cavity and a flange extending outward from said cavity, said inner container flange being of a dimension to fit into said stepped recess of said outer container,
   an insert member sized to fit into said inner container cavity, said insert member defining a linear depression therein in the form of a stepped arcuate groove to hold a tissue implant form;
   a permeable cover sealed to the flange of the inner container covering said inner container cavity; and
   an impermeable outer cover sealed to the flange of the outer container covering said outer container cavity.

8. A double sterile package container as claimed in claim 7 wherein said insert member housing defines a second arcuate groove which intersects said first stepped groove.

9. A sterile package for storing sterile allograft tissue implant forms comprising:
   an insert container defining an open faced cavity and a flange extending outward from said cavity,
   an insert member sized to fit into said inner container cavity, said insert member comprising a housing defining a curved groove with stepped ends forming shoulders to hold a tissue implant form, and at least one other groove intersecting at least a portion of said curved groove; and
   a removable cover sealed to the flange of the insert container covering said insert container cavity.

10. A container assembly for storing sterile allograft tissue implant forms in a sterile condition comprising:
    an outer container defining an open faced cavity and a flange extending outward from said cavity, a stepped recess formed in said flange surrounding said cavity;
    an inner container defining an open faced cavity and a flange extending outward from said cavity, said inner container flange being of a dimension to fit into said stepped recess of said outer container,
    an insert member sized to fit into said inner container cavity, said insert member defining a shaped structure therein to hold a tissue implant form;
    a permeable cover sealed to the flange of the inner container covering said inner container cavity;
    an outer cover sealed to the flange of the outer container covering said outer container cavity; and
    both flanges of said outer container and said inner container having one end which extends outward further than the other portions of said flange to form a handle for the respective container.

11. A container assembly as claimed in claim 10 wherein of said handle has a grasping rib formed thereon.

* * * * *